US009610418B2

(12) United States Patent
Rothermel et al.

(10) Patent No.: US 9,610,418 B2
(45) Date of Patent: Apr. 4, 2017

(54) PATIENT INTERFACE DEVICE INCLUDING A PNEUMATICALLY ADJUSTING FOREHEAD SUPPORT

(75) Inventors: Justin Edward Rothermel, Monroeville, PA (US); Chad Zediker, Greensbug, PA (US); Robert Earl Hieber, IV, Export, PA (US); Christopher James Kadamus, Jamaica Plains, PA (US); Richard Thomas Haibach, Verona, PA (US); Keith Aaron Grider, Chicago, IL (US); Arvin Abadilla, Somerville, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 253 days.

(21) Appl. No.: 14/115,429

(22) PCT Filed: May 10, 2012

(86) PCT No.: PCT/IB2012/052325
§ 371 (c)(1),
(2), (4) Date: Nov. 4, 2013

(87) PCT Pub. No.: WO2012/153289
PCT Pub. Date: Nov. 15, 2012

(65) Prior Publication Data
US 2014/0076323 A1   Mar. 20, 2014

Related U.S. Application Data

(60) Provisional application No. 61/485,234, filed on May 12, 2011.

(51) Int. Cl.
*A61M 16/06* (2006.01)
*A61M 16/00* (2006.01)

(52) U.S. Cl.
CPC .... *A61M 16/0683* (2013.01); *A61M 16/0057* (2013.01); *A61M 16/06* (2013.01); *A61M 16/0633* (2014.02); *A61M 16/0644* (2014.02)

(58) Field of Classification Search
CPC .......... A61M 16/0683; A61M 16/0057; A61M 16/0644; A61M 16/0633; A61M 16/06;
(Continued)

(56) References Cited

U.S. PATENT DOCUMENTS 5,158,767 A * 10/1992 Cohen ................. A43B 5/0407
36/114
2004/0216746 A1   11/2004 Jones, Jr.
(Continued)

FOREIGN PATENT DOCUMENTS

CN   101155618 A   4/2008
CN   101282767 A   10/2008
(Continued)

*Primary Examiner* — Peter S Vasat
*Assistant Examiner* — Margaret Luarca
(74) *Attorney, Agent, or Firm* — Michael W. Haas (57) ABSTRACT

A patient interface device (8) includes a patient sealing assembly (12) adapted to communicate a flow of breathing gas within an airway of a patient, the patient sealing assembly including a cushion (14), a frame member (16) coupled to the cushion, and an adjustable forehead support assembly (26) coupled to the frame member. The adjustable forehead support assembly includes a forehead cushion (30) and an inflatable and deflatable bladder (48) coupled to the forehead cushion, wherein inflation and deflation of the bladder causes the distal end (24) of the frame member to move relative to the forehead cushion in a manner wherein a pressure applied to a bridge of a nose of the patient by the cushion is adjusted.

6 Claims, 6 Drawing Sheets

(58) Field of Classification Search
CPC .......... A61M 16/0622; A61M 16/0627; A61M 16/0638; A61M 16/065
USPC .......................... 128/205.25, 206.24, 207.11
See application file for complete search history.

(56) References Cited

U.S. PATENT DOCUMENTS

| | | | |
|---|---|---|---|
| 2007/0107733 A1* | 5/2007 | Ho | A61M 16/06 128/206.24 |
| 2007/0131717 A1* | 6/2007 | Davies | A61M 15/009 222/162 |
| 2007/0163594 A1 | 7/2007 | Ho et al. | |
| 2007/0215161 A1* | 9/2007 | Frater | A61M 16/06 128/206.24 |
| 2011/0180070 A1* | 7/2011 | Ho | A61M 16/06 128/204.18 |

FOREIGN PATENT DOCUMENTS

| | | |
|---|---|---|
| EP | 2005985 A2 | 12/2008 |
| WO | WO2004078231 A2 | 9/2004 |
| WO | WO2005009521 A1 | 2/2005 |
| WO | WO2005094928 A1 | 10/2005 |
| WO | WO2005123166 A1 | 12/2005 |
| WO | WO2006113321 A2 | 10/2006 |
| WO | WO2007021777 A2 | 2/2007 |
| WO | WO2007143793 A1 | 12/2007 |

* cited by examiner

PATIENT INTERFACE DEVICE INCLUDING A PNEUMATICALLY ADJUSTING FOREHEAD SUPPORT

CROSS-REFERENCE TO RELATED APPLICATIONS

This patent application claims the priority benefit under 35 U.S.C. §371 of international patent application no. PCT/IB2012/052325, filed May 10, 2012, which claims the priority benefit under 35 U.S.C. §119(e) of U.S. Provisional Application No. 61/485,234 filed on May 12, 2011, the contents of which are herein incorporated by reference.

BACKGROUND OF THE INVENTION

1. Field of the Invention

The present invention relates to patient interface devices for transporting a gas to and/or from an airway of a user, and in particular, to a patient interface device including a mechanism for pneumatically adjusting a forehead support of the patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Because such patient interface devices are typically worn for an extended period of time, it is important for the headgear to maintain the mask component of the device in a tight enough seal against the patient's face without discomfort. One area where fit and comfort is often a concern is the bridge of the patient's nose, as most patient interface devices will apply a pressure to this area. If this pressure is not able to be managed effectively, either or both of a poor fit or patient discomfort will result, thereby limiting the effectiveness of the device.

SUMMARY OF THE INVENTION

Accordingly, it is an object of the present invention to provide a patient interface device that overcomes the shortcomings of conventional patient interface devices. This object is achieved according to one embodiment of the present invention by providing a patient interface device that includes a selectively adjustable forehead support assembly that allows for simple and convenient management of the nose bridge pressure that is applied by the patient interface device.

In one embodiment, a patient interface device is provided that includes a patient sealing assembly adapted to communicate a flow of breathing gas within an airway of a patient. The patient sealing assembly includes a cushion, a frame member coupled to the cushion, and an adjustable forehead support assembly coupled to the frame member. The adjustable forehead support assembly includes a forehead cushion and a selectively inflatable and deflatable bladder coupled to the forehead cushion, wherein inflation and deflation of the bladder causes the distal end of the frame member to move relative to the forehead cushion in a manner wherein a pressure applied to a bridge of a nose of the patient by the cushion is adjusted.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
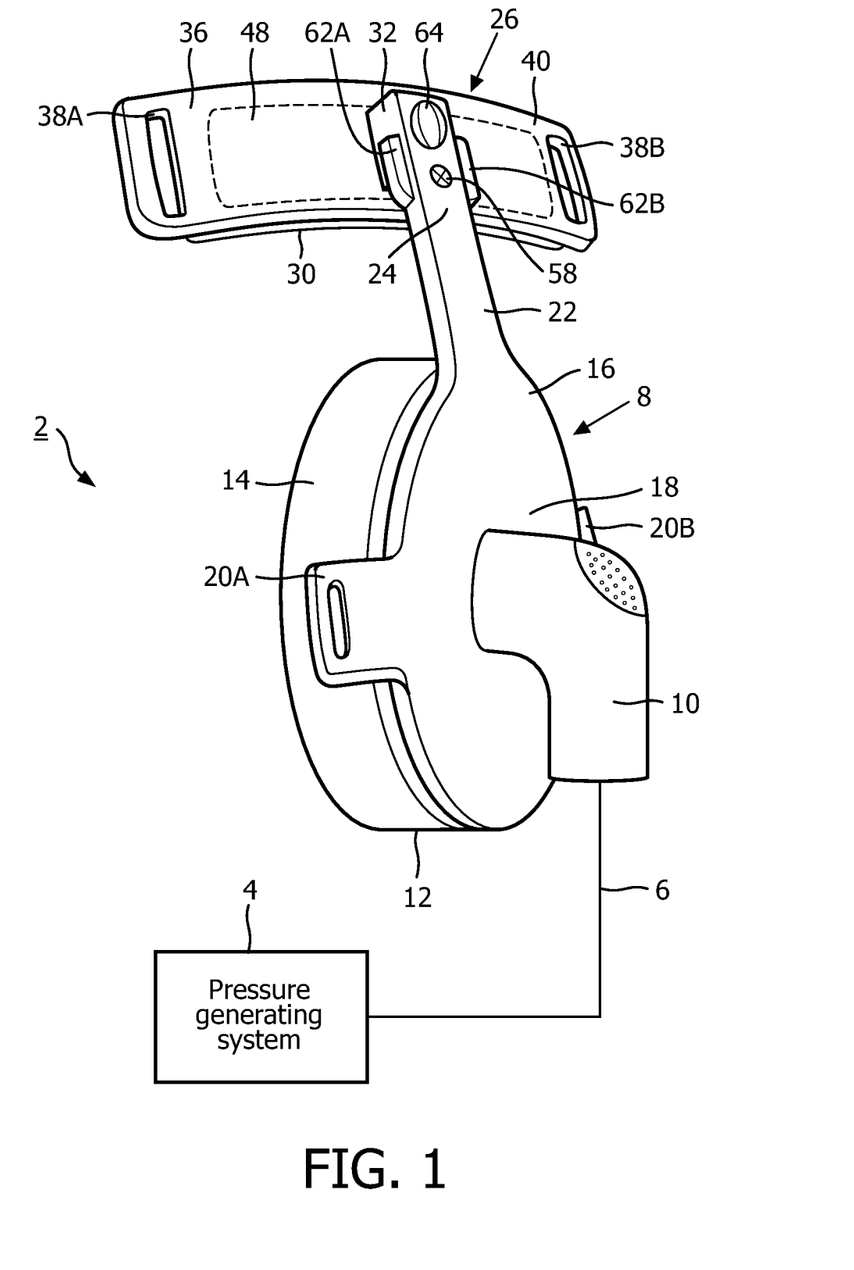
FIG. 1 is a schematic diagram of a system adapted to provide a regimen of respiratory therapy to a patient according to one exemplary embodiment of the present invention.

A system 2 adapted to provide a regimen of respiratory therapy to a patient according to one exemplary embodiment is generally shown in FIG. 1. System 2 includes a pressure generating device 4, a delivery conduit 6, and a patient interface device 8 having a fluid coupling conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex® or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

Patient interface device 8 includes a patient sealing assembly 12, which in the illustrated embodiment is a nasal/oral mask. However, other types of patient sealing assemblies, such as, without limitation, a nasal mask or a nasal cushion, which facilitates the delivery of the flow of breathing gas to the airway of a patient, may be substituted for patient sealing assembly 12 while remaining within the scope of the present invention. Patient sealing assembly 12 includes a cushion 14 coupled to a frame member 16. In the illustrated embodiment, cushion 14 is defined from a unitary piece of soft, flexible, cushiony, elastomeric material, such as, without limitation, silicone, an appropriately soft thermoplastic elastomer, a closed cell foam, a gel or any combination of such materials. Also in the illustrated embodiment, frame member 16 is made of a rigid or semi-rigid material, such as, without limitation, an injection molded thermoplastic or silicone, and includes a faceplate portion 18 to which cushion 14 is fluidly attached. An opening in faceplate portion 18, to which fluid coupling conduit 10 is coupled, allows the flow of breathing gas from pressure generating device 4 to be communicated to an interior space defined by cushion 14, and then to the airway of a patient. In an alternative embodiment, cushion 14 may be supported by and received through an orifice provided in frame member 16 so that fluid coupling conduit 10 can be directly connected to cushion 14 rather than to a faceplate portion. In addition, in the exemplary embodiment, faceplate portion 18 includes first and second connecting members 20A, 20B for receiving a respective strap of a headgear component (not shown) to secure patient interface device 8 to the patient's head.

Figure 2:
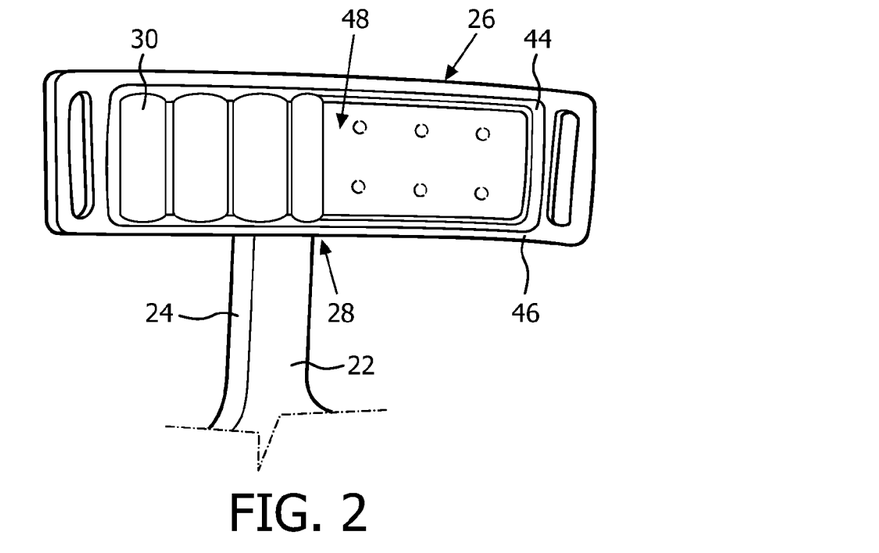
FIG. 2 is a rear elevational view and FIG. 3 is a schematic cross-sectional illustration showing an exemplary adjustable forehead support assembly of the patient interface device of the system of FIG. 1.
Figure 3:
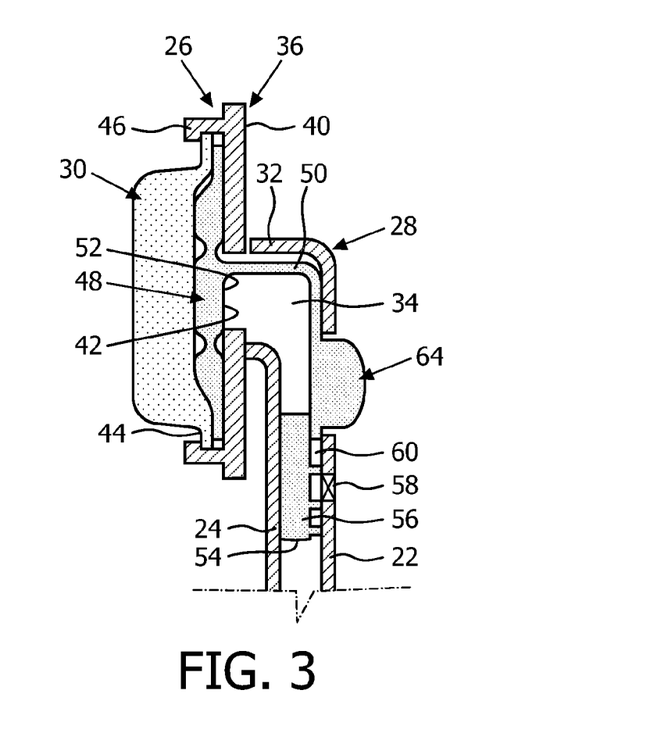

Frame member 16 also includes an elongated connecting member 22 having a distal end 24 that is connected to an adjustable forehead support assembly 26 of patient interface device 8. FIG. 2 is a rear elevational view and FIG. 3 is a schematic cross-sectional illustration showing the exemplary embodiment of adjustable forehead support assembly 26 and distal end 24 of connection member 22 of patient interface device 8. Adjustable forehead support assembly 26 includes an adjustment mechanism 28 that is coupled to a forehead cushion 30 (shown in partial cut-away form in FIG. 2), of cushion 14. As described in detail herein, adjustment mechanism 28 provides a mechanism for selectively adjusting the force applied to the bridge of the nose of a patient by an apex portion of cushion 14 by varying the position of connecting member 22, and in particular distal end 24 thereof, with respect to forehead cushion 30.

In the illustrated embodiment, adjustment mechanism 28 includes a stabilizing arm portion 32 provided at distal end 24 of connecting member 22. As seen in FIG. 3, stabilizing arm portion 32 defines an inner chamber 34. While in the illustrated embodiment stabilizing arm portion 32 is formed as an integral part of distal end 24, it may in alternative embodiments be formed separately and attached to distal end 24 by a suitable mechanism such as an adhesive.

Adjustment mechanism 28 further includes a forehead cushion support member 36 to which forehead cushion 30 is attached. Forehead cushion support member 36 is made of a rigid or semi-rigid material, such as, without limitation, an injection molded thermoplastic or silicone, and includes first and second loop connectors 38A, 38B structured to receive a respective upper strap of a headgear component (not shown) to help secure patient interface device 8 to the patient's head. Forehead cushion support member 36 has a front surface 40 to which stabilizing arm portion 32 is attached. As seen in FIG. 3, front surface 40 has a front orifice 42 that is mated with stabilizing arm portion 32.

As seen in FIGS. 2 and 3, a recess 44 is provided in a rear surface 46 of forehead cushion support member 36. Adjustment mechanism 28 also includes an expandable, inflatable bladder 48 that is positioned in recess 44 in between forehead cushion 30 and forehead cushion support member 36. As described in greater detail herein, bladder 48 is structured to be selectively inflated and deflated using a fluid such as air. In the exemplary embodiment, bladder 48 has a shape that generally matches the shape of forehead cushion support member 36 (e.g., a rectilinear shape) and is made of a flexible material such as, without limitation, silicone, rubber, foam, fabric, a thermoplastic or thermoset material, or a combination of such materials.

As seen in FIG. 3, a fluid conduit 50 is fluidly coupled to and extends from the front side 52 of bladder 48 and into inner chamber 34. Adjustment mechanism 28 also includes a bladder pump 54 shown schematically in FIG. 3. Bladder pump 54 is fluidly coupled to bladder 38 through fluid conduit 50. Bladder pump 54 is structured to manually cause air to be drawn from the surrounding atmosphere and pumped into bladder 48 to cause bladder 48 to expand. Manual air pumps are well known in the art, and thus bladder pump 54 may be in the form of any of a number of known or later developed pump configurations. In the illustrated embodiment, bladder pump 54 includes a bulb member 56 made of a flexible material such as latex rubber or silicone, and includes a one way air intake check valve 58 coupled to atmosphere, a one way air exit check valve 60 coupled to fluid conduit 50, and actuator paddles 62A, 62B (FIG. 1) that are provided on opposite sides of stabilizing arm portion 32. When actuator paddles 62A, 62B are depressed, they exert a squeezing force on bulb member 56, which in turn causes air that is trapped in bulb member 56 to be forced out the air exit check valve 60 and into bladder 48, thereby causing bladder 48 to expand.

When the pressure exerted on bulb member 56 by actuator paddles 62A, 62B is released, air is sucked into bulb member 56 through the air intake check valve 58 from the surrounding atmosphere as bulb member 56 returns to its resting shape. In addition, adjustment mechanism 28 further includes a pressure relief mechanism 64, shown schematically in FIG. 3, that is coupled to fluid conduit 50. When pressure relief mechanism 64 is actuated, it allows air to escape from bladder 48 to atmosphere so that bladder 48 may be selectively deflated. In the exemplary embodiment, pressure relief mechanism 64 includes a one way valve with a pressure relief actuator (e.g., button) for actuating the valve.

Thus, as just described, bladder 48 may be selectively inflated (expanded) and deflated (contracted) through selective operation of bladder pump 54 and pressure relief mechanism 64. Such expansion and contraction of bladder 48 will cause the position of forehead cushion support member 36, and thus connecting member 22, relative to forehead cushion 30 (which will be at a fixed position on the patient's head) to be linearly adjusted. This linear adjustment action allows for selective adjustment of the force that is applied to the bridge of the patient's nose by the apex portion of cushion 14 because varying the position of connecting member 22 as just described will cause the apex portion of cushion 14 to rotate toward and away from the patient's nose.

Figure 4:
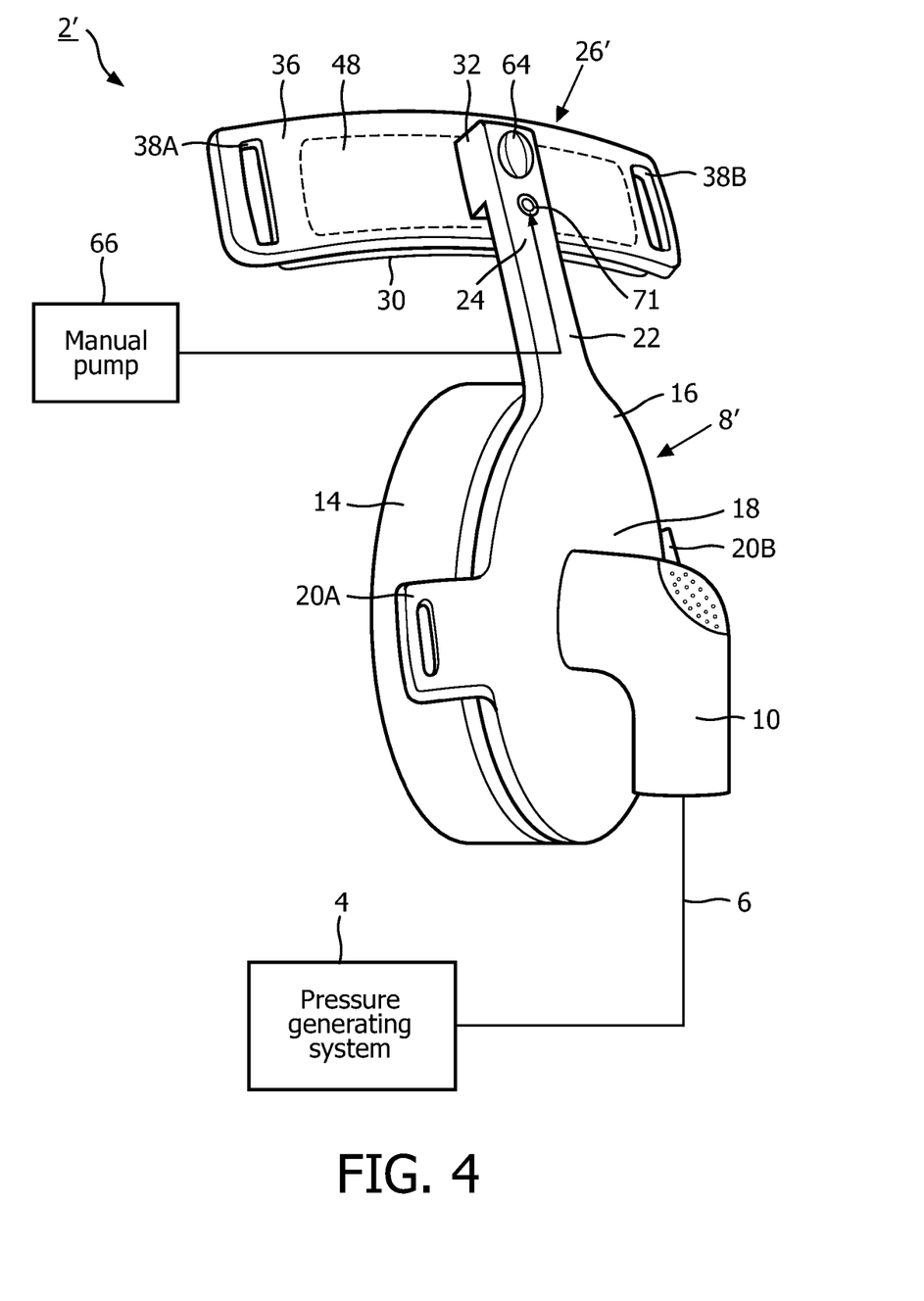
FIG. 4 is a schematic diagram of a system adapted to provide a regimen of respiratory therapy to a patient according to an alternative exemplary embodiment of the present invention.

A system 2' adapted to provide a regimen of respiratory therapy to a patient according to an alternative exemplary embodiment is generally shown in FIG. 4. System 2' includes many of the same components as system 2, and thus like components are labeled with like reference numerals. System 2' includes an alternative patient interface device 8' having an alternative adjustable forehead support assembly 26'. Like adjustable forehead support assembly 26, adjustable forehead support assembly 26' includes an inflatable bladder 48 that is positioned in between forehead cushion 30 and forehead cushion support member 36. However, rather than being selectively inflated using bladder pump 54, inflatable bladder 48 of adjustable forehead support assembly 26' may be selectively inflated using a separate manual pump 66 (e.g., a bulb or piston type manual air pump) that is structured to be coupled to bladder 48 through a one way inflation valve 71 provided on stabilizing arm portion 32. As was the case with adjustable forehead support assembly 26, bladder 48 in adjustable forehead support assembly 26' may be deflated through actuation of pressure relief mechanism 64.

Figure 5:
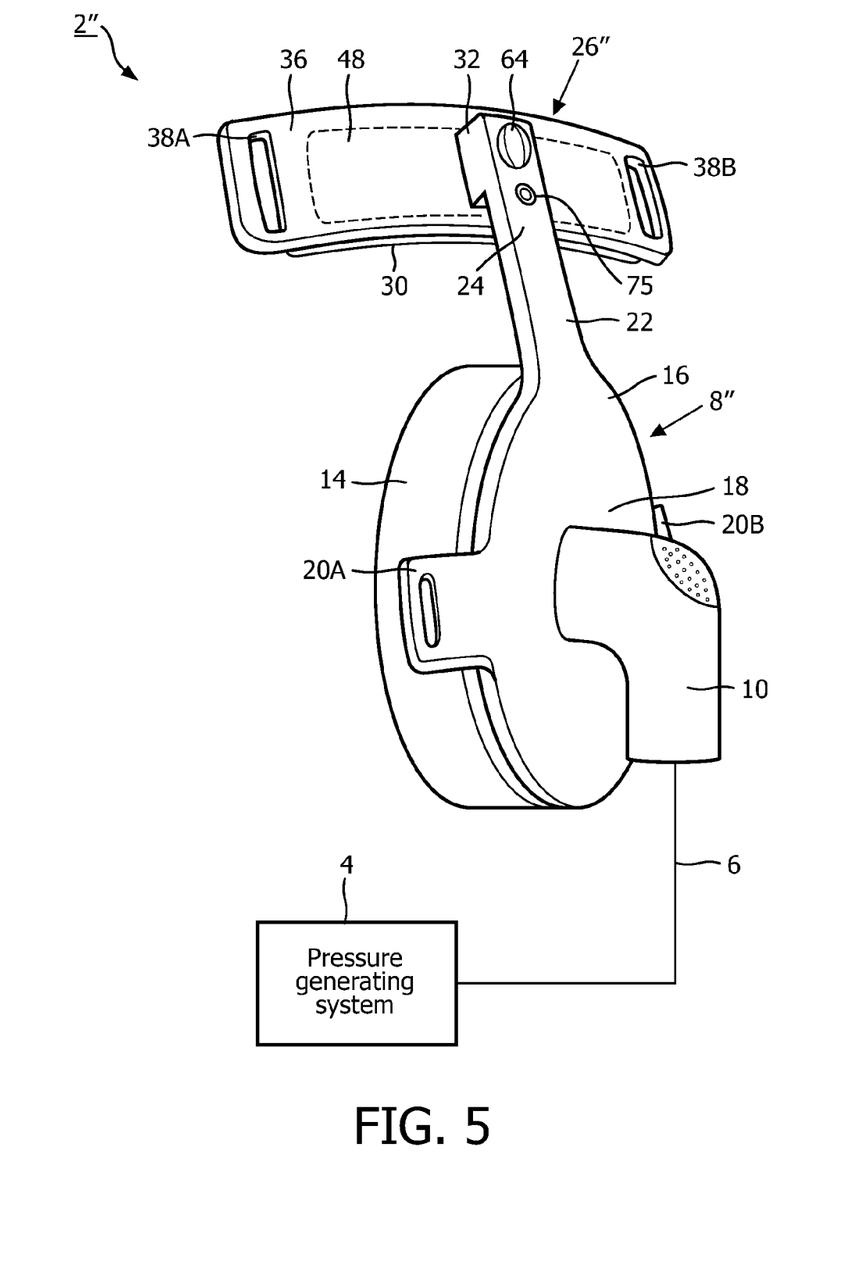
FIG. 5 is a schematic diagram of a system adapted to provide a regimen of respiratory therapy to a patient according to another alternative exemplary embodiment of the present invention.
Figure 6:
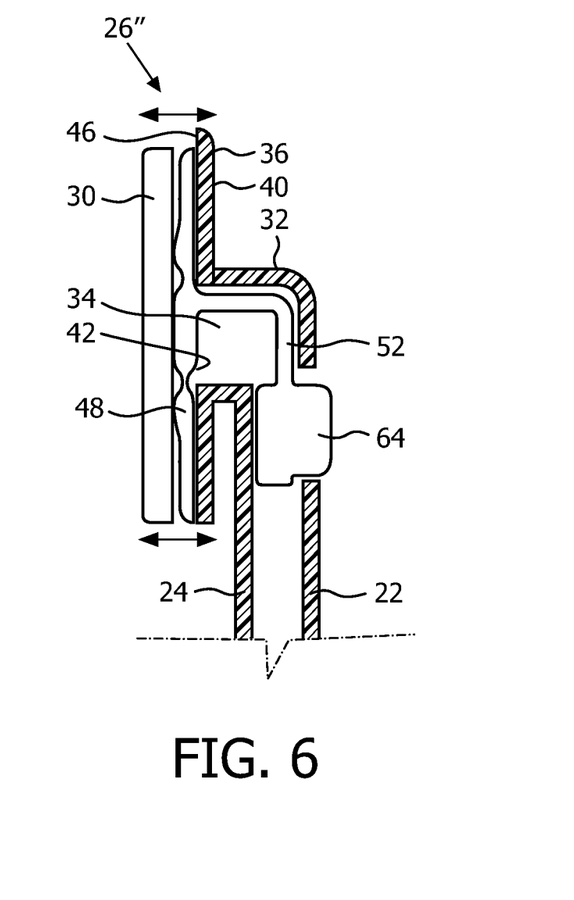
FIG. 6 is a schematic cross-sectional illustration showing an exemplary adjustable forehead support assembly of the patient interface device of the system of FIG. 5.

A system 2" adapted to provide a regimen of respiratory therapy to a patient according to another alternative exemplary embodiment is generally shown in FIG. 5. System 2" includes many of the same components as system 2, and thus like components are labeled with like reference numerals. System 2" includes an alternative patient interface device 8" having an alternative adjustable forehead support assembly 26". FIG. 6 is a schematic cross-sectional illustration showing adjustable forehead support assembly 26" and distal end 24 of connection member 22 of patient interface device 8". Like adjustable forehead support assemblies 26 and 26' described elsewhere herein, adjustable forehead support assembly 26" includes an inflatable bladder 48. In addition, as seen in FIG. 5, a one way air intake valve 75 coupled to bladder 48 is provided on stabilizing arm portion 32. The purpose of one way air intake valve 75 is described below.

As seen in FIG. 6, inflatable bladder 48 is positioned in between forehead cushion 30 and forehead cushion support member 36 in a manner wherein a first side of bladder 48 is attached to forehead cushion support member 36 and a second side of blabber 48 is attached to forehead cushion 48. However, rather than being selectively inflated using bladder pump 54 or manual pump 66, inflatable bladder 48 of adjustable forehead support assembly 26" may be selectively inflated by pulling on stabilizing arm portion 32 and moving it relative to forehead cushion 30 (see arrows in FIG. 6). This action will cause air to be drawn into bladder 48 through one way air intake valve 75 with the resulting expansion of bladder 48. As was the case with adjustable forehead support assembly 26, bladder 48 in adjustable forehead support assembly 26" may be deflated through actuation of pressure relief mechanism 64.

Figure 7:
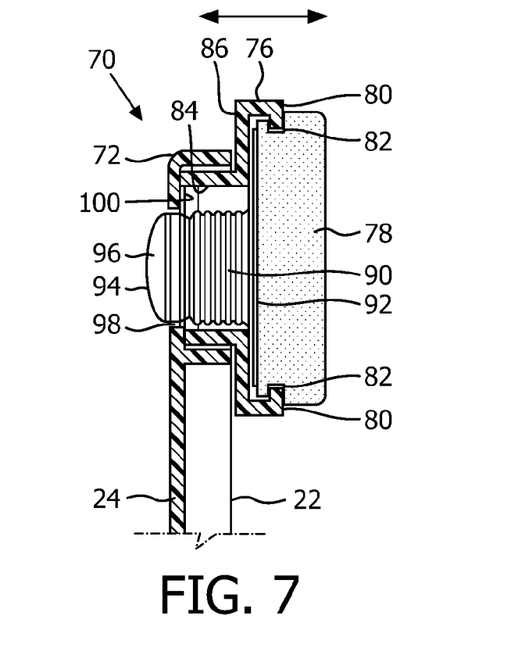
FIGS. 7 and 8 are schematic cross-sectional illustrations showing an alternative exemplary adjustable forehead support assembly that may be used in the patient interface device of the system of FIG. 5.
Figure 8:
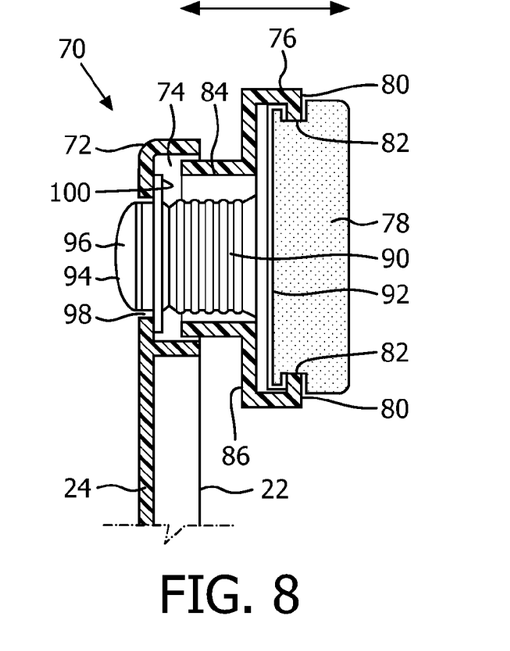

FIGS. 7 and 8 are schematic cross-sectional illustrations showing an adjustable forehead support assembly 70 according to an alternative embodiment of the present invention. Adjustable forehead support assembly 70 may be substituted for adjustable forehead support assembly 26" in system 2" and distal end 24 of connection member 22 of patient interface device 8". FIG. 7 shows adjustable forehead support assembly 70 is a compressed and deflated condition and FIG. 8 shows adjustable forehead support assembly 70 is an expanded and inflated condition, both of which are described below.

In the illustrated embodiment, adjustment mechanism 70 includes a stabilizing arm portion 72 provided at distal end 24 of connecting member 22. While in the illustrated embodiment stabilizing arm portion 72 is formed as an integral part of distal end 24, it may in alternative embodiments be formed separately and attached to distal end 24 by a suitable mechanism such as an adhesive. As best seen in FIG. 8, stabilizing arm portion 72 defines an inner chamber 74, the function of which is described in greater detail below.

Adjustment mechanism 70 further includes a forehead cushion support member 76 to which a forehead cushion 78 is attached. Forehead cushion support member 76 is made of a rigid or semi-rigid material, such as, without limitation, an injection molded thermoplastic or silicone, forehead cushion 78 is made of a material that is similar to the material of forehead cushion 30. Forehead cushion support member 76 includes rear flanges 80 that are received within grooves 82 provided in an outer surface of forehead cushion 78 in order to couple the two components together. In addition, a sleeve member 84 extends outwardly from a front surface 86 of forehead cushion support member 76.

Adjustment mechanism 70 also includes an inflatable bladder 90 which is attached to a front surface 92 of forehead cushion 78 and which extends into sleeve member 84. As described in greater detail herein, inflatable bladder 90 is structured to be selectively inflated and deflated. In the exemplary embodiment, inflatable bladder 90 is made of a flexible material such as, without limitation, silicone, rubber, foam, fabric, a thermoplastic or thermoset material, or a combination of such materials, and has a bellowed configuration. In addition, as seen in FIGS. 7 and 8, sleeve member 84 is slideably received within inner chamber 74 such that inflatable bladder 90 is also received within inner chamber 74.

Furthermore, adjustment mechanism 70 includes a valve mechanism 94 that is coupled to inflatable bladder 90. In the exemplary embodiment, valve mechanism 94 includes a two way valve with an actuator 96 (e.g., button) for actuating the valve that extends through an orifice 98 provided in stabilizing arm portion 72. Rather than being selectively inflated using a separate pump (e.g., bladder pump 54 or manual pump 66), inflatable bladder 90 may be selectively inflated by actuating valve mechanism 94 (in the exemplary embodiment this is done by pressing the button 96) and pulling on stabilizing arm portion 72 and moving it away from forehead cushion 78 (see arrows in FIGS. 7 and 8; sleeve member 84 will slide within inner chamber 74). This action will cause expansion of bladder 90 as shown in FIG. 8 (bladder 90 includes a top flange 100 that engages the inside of stabilizing arm portion 72) such that air is drawn into bladder 90 through valve mechanism 94. In addition, bladder 90 may be deflated by actuating valve mechanism 94 and pushing on stabilizing arm portion 72 and moving it toward forehead cushion 78. This action will cause air to be expelled from bladder 90 through valve mechanism 94 with the resulting compression of bladder 90 as shown in FIG. 7.

Thus various embodiments of a patient interface device have been provided herein that each include a pneumatically adjustable forehead support assembly. In each case, the adjustable forehead support assembly allows for simple and convenient management of the nose bridge pressure that is applied by the patient interface device by selectively adjusting the position of the frame of the patient interface device to the forehead cushion of the patient interface device.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A patient interface device, comprising:
a patient sealing assembly adapted to communicate a flow of breathing gas within an airway of a patient, the patient sealing assembly including a cushion and a frame member coupled to the cushion;
an adjustable forehead support assembly operatively coupled to a distal end of the frame member, the adjustable forehead support assembly including a forehead cushion, and a selectively inflatable and deflatable bladder coupled to the forehead cushion;
a pump structured to selectively pump a medium into the bladder in order to inflate the bladder, wherein the pump is provided within a housing member provided at the distal end of the frame member and includes a bulb member fluidly coupled to the bladder; and
at least one actuating member provided on an outside of the housing member and structured to apply a squeezing force to the bulb member to cause the medium trapped in the bulb member to be provided to the bladder, and wherein inflation and deflation of the bladder causes the distal end of the frame member to move relative to the forehead cushion in a manner wherein a pressure applied to a bridge of a nose of the patient by the cushion is adjusted.

2. The patient interface device according to claim 1, the adjustable forehead support assembly including a forehead cushion support member coupled to the forehead cushion, wherein the bladder is provided in between the forehead cushion and the forehead cushion support member, wherein inflation and deflation of the bladder causes the forehead cushion support member to move relative to the forehead cushion, and wherein movement of the forehead cushion support member relative to the forehead cushion causes movement of the frame member relative to the forehead cushion in a manner wherein a pressure applied to a bridge of a nose of the patient by the cushion is adjusted.

3. The patient interface device according to claim 1, wherein the at least one actuating member comprises first and second paddle members provided on opposite sides of the housing member.

4. The patient interface device according to claim 1, further comprising a pressure relief mechanism provided on the housing member, the pressure relief mechanism being structured to selectively cause the medium to be released from the bladder to deflate the bladder.

5. A method of adjusting a patient interface device having a patient sealing assembly adapted to communicate a flow of breathing gas within an airway of a patient, the patient sealing assembly including a cushion and a frame member coupled to the cushion, an adjustable forehead support assembly operatively coupled to a distal end of the frame member, the adjustable forehead support assembly including a forehead cushion and a selectively inflatable and deflatable bladder coupled to the forehead cushion support member, a pump structured to selectively pump a medium into the bladder in order to inflate the bladder, wherein the pump is provided within a housing member provided at the distal end of the frame member and includes a bulb member fluidly coupled to the bladder, and at least one actuating member provided on an outside of the housing member and structured to apply a squeezing force to the bulb member to cause the medium trapped in the bulb member to be provided to the bladder, the method comprising:
inflating the bladder by actuating the at least one actuating member and causing the distal end of the frame member to move in a direction away from the forehead cushion such that a pressure applied to a bridge of a nose of the patient by the cushion is decreased; and
deflating the bladder and causing the distal end of the frame member to move in a direction toward the forehead cushion such that the pressure applied to the bridge of the nose of the patient by the cushion is increased.

6. The method according to claim 5, wherein the at least one actuating member comprises first and second paddle members provided on opposite sides of the housing member, wherein the inflating the bladder comprises actuating the first and second paddle members in opposite directions.

* * * * *